US006383481B1

(12) United States Patent
Ikehara et al.

(10) Patent No.: US 6,383,481 B1
(45) Date of Patent: May 7, 2002

(54) METHOD FOR TRANSPLANTATION OF HEMOPOIETIC STEM CELLS

(75) Inventors: Susumu Ikehara, Osaka; Muneo Inaba, Kyoto; Kenji Takeuchi, Osaka; Taketoshi Kushida, Amagasaki, all of (JP)

(73) Assignee: Japan Immunoresearch Laboratories Co., Ltd., Gunma-Ken (JP)

( * ) Notice: Subject to any disclaimer, the term of this patent is extended or adjusted under 35 U.S.C. 154(b) by 0 days.

(21) Appl. No.: 09/265,418

(22) Filed: Mar. 10, 1999

(30) Foreign Application Priority Data

Mar. 30, 1998 (JP) ............................................ 10-084275

(51) Int. Cl.$^7$ ............................ A61K 35/28; C12N 5/06
(52) U.S. Cl. .................. 424/93.1; 424/93.7; 424/93.71; 424/93.73; 435/325; 435/372
(58) Field of Search ............................ 424/93.21, 93.1, 424/93.7, 93.71, 93.73; 435/375, 325, 372; 128/898

(56) References Cited

FOREIGN PATENT DOCUMENTS

| WO | WO 98/21313 A | 5/1998 |
| WO | WO 98/39016 A | 9/1998 |

OTHER PUBLICATIONS

Kamei, T. et al. Intravenous and Portal Venous Administration of Modified Donor Antigen Prolongs Rat Parathyroid Allograft Survival Surgery, 106:1028–35, 1989.*
Kamei T. et al. Pretransplant Portal Venous Administration of Donor Antigen and Portal Venous Allograft Drainage Synergistically Prolong Rat Cardiac Allograft Survival, Surgery 108: 415–22, 1990.*
Alberto M. Marmont, Perspective, Immuneablation with Stem–Cell Rescue: A Possible Cure for Systemic Lupus Erythematosus?Lupus, 2(3) 151–156, 1993.*
Kim, Testunan et al, "Induction of immunological tolerance by portal administration of bone marrow cells and splenocytes—Development of a new organ transplantation technique,", translated abstract, *The Japanese Society of Pathology*, III–PA–80, (1998).
Han, Tensetus et al., "Allogenic bone marrow transplantation: Comparison of intravenous (IV) vs. portal (PV) administration", translated abstract, *The Japanese Society of Pathology*, III–PA–79, (1998).
Takeuchi, Kenji et al., "Bone marrow transplantation to radiation–sensitive MRL/lpr mice: a novel therapy of autoimmune diseases", translated abstract, *Proceedings of the Japanese Society for Immunology*, vol. 27, 3P62, (1997).
Morita, Haruo et al., "Induction of immunological tolerance by portal administration of bone marrow cells—Development of a new organ transplantation technique", translated abstract, *Proceedings of the Japanese Society for Immunology*, vol. 27, 3K2, (1997).

Y. Zhang, et al. "Fate of allogeneic or syngeneic cells in intravenous or portal vein injection: possible explanation for the mechanism of tolerance induction by portal vein injection," Eur. J. Immunol. 24: 1558–1565 (1994).
K. Takeuchi, et al. "A New Strategy for Treatment of Autoimmune Diseases in Chimeric Resistant MRL/lpr Mice," Blood, 91:4616–4623 (Jun. 15, 1998).
T. Ishida, et al., "Requirement of Donor–Derived Stromal Cells in the Bone Marrow for Successful Allogeneic Bone Marrow Transplantation: Complete Prevention of Recurrence of Autoimmune Diseases in MRL/MP–lpr/lpr Mice by Transplanation of Bone Marrow Plus Bones (Stromal Cells) from the Same Donor," J. Immunol. 152:3119–3127 (1994).
S. Ikehara, "Autoimmune diseasses as stem cell disorders: Normal stem cell transplant for their treatment (Review)," Int'l. J. Molec. Med. 1:5–16 (1998).
K. Sugiura, et al., "Induction of Donor–Specific T Cell Anergy by Portal Venous Injection of Allogeneic Cells," Immunobiol., 197:460–477 (1997).
A. Eid, et al., "Induction of transplantation tolerance by intraportal injectin of allogeneic bone marrow cells. Possible implications for intrauterine bone marrow transplantation across major histocompatibility barriers." Transplantation International 1:109–112 (Jul. 1988) (XP000872310 Abstract).
R. M. Gorczynski, et al., "Prolongation of rat small bowel or renal allograft survival by pretransplant transfusion and/or by varying the route of allograft venous drainage." Transplantation 58: (7) 816–820 (Oct. 15, 1994) (XP000872326 Abstract).
N. Yoshimura, et al, "The effects of perioperative portal venous inoculation with donor lymphocytes on renal allograft survival in the rat. Specific prolongation of donor grafts and suppressor factor in the serum", Transplantation, 49:167–171, (Jan. 1990).
H. Morita, et al., "A strategy for organ allografts without using immunosuppressants or irradiation" Proc. National Academy. Sci., U.S.A. 95:6947–6952 (Jun. 1998) (XP000872835 whole document).
T. Kushida, et al., "Treatment of intractable autoimmune diseases in MRL/lpr mice using a new strategy for allogeneic bone marrow transplantation," Blood 95:1862–1868, (Mar. 1, 2000).

* cited by examiner

Primary Examiner—Michael C. Wilson
(74) Attorney, Agent, or Firm—Sughrue Mion, PLLC

(57) ABSTRACT

This invention relates to a method of transplanting hemopoietic stem cells which Comprises subjecting a recipient to a radiation treatment using an effective exposure dose for hemopoietic stem cell transplantation in advance and administering hemopoietic stem cells from a donor from the portal vein. By this method the graft failure/rejection of donor cells can be avoided to thereby maintain the transplant in satisfactory condition.

2 Claims, 1 Drawing Sheet

METHOD FOR TRANSPLANTATION OF HEMOPOIETIC STEM CELLS

TECHNICAL FIELD

This invention relates to a method of transplanting hemopoietic stem cells, and more particularly to a novel method of transplanting hemopoietic stem cells by which donor cells may be well sustained without graft failure/rejection.

PRIOR ART AND PROBLEMS THEREOF

In the so-called modern bone marrow transplantation (BMT), an HLA-matched individual is recruited as the marrow donor and the recipient, i.e. patient, is placed on a full-fledged immunosuppressive regimen for preventing graft rejection in a pathogen-free environment until post-transplantation hemoimmunological recovery has taken place. In recent years, the source of pluripotent hemopoietic stem cells, the true subject of a BMT, has been expanding from the bone marrow of an HLA-matched individual or a partially HLA-mismatched individual, autologous bone marrow, autologous peripheral blood, allogeneic peripheral blood and cord blood. To keep abreast of this expansion, the transplantation of purified pluripotent hemopoietic stem cells available from such sources has become feasible and said BMT is now subsumed in the expanded concept of hemopoietic stem cell transplantation.

By now the bone marrow recipient has come to include patients with aplastic anemia, leukemia, certain hereditary diseases, and even solid tumors such as malignant lymphoma and carcinoma of the breast and, in fact, said hemopoietic stem cell transplantation is currently performed in a broad spectrum of diseases.

For detailed information on such hemopoietic stem cell transplantations, "Hemopoietic Stem Cell Transplantation, Its Foundation and Clinical Practice" [Modern Medicine, Special Issue, 53, 2, 1998] can be consulted and the descriptions given there are incorporated in this specification by reference.

Furthermore, autoimmune diseases have come to be regarded as stem cell disorders in recent years [International Journal of Molecular Medicine, 1:5–16, 1998] and treatment of various autoimmune diseases by BMT, particularly allogeneic bone marrow transplantation (allo-BMT), is a focus of attention today.

Playing a central role in the recent diversification of BMT is allo-BMT. Particularly in keeping abreast of the expansion and improved coordination of bone marrow banks, the number of cases receiving unrelated donor-host BMT is on a steady increase and countermeasures to graft failure/rejection and graft-versus-host disease (GVHD) as well as the effect of transplantation are the current subjects of debate and study.

The object of this invention is to provide a novel method of transplanting hemopoietic stem cells which overcomes the long-standing problems associated with hemopoietic stem cell transplantation, particularly the problem of graft failure/rejection.

DISCLOSURE OF THE INVENTION

In accordance with this invention there is provided a method of transplanting hemopoietic stem cells which comprises subjecting a graft recipient to a radiation treatment using an effective exposure dose for hemopoietic stem cell transplantation in advance and then transplanting hemopoietic stem cells from a graft donor via the portal vein.

The present invention further provides said transplantation method further comprising administering hemopoietic stem cells intravenously following the portal venous administration of hemopoietic stem cells; said transplantation method wherein the radiation treatment is carried out by total body irradiation using two divided doses a day; and said transplantation method which is used for the treatment of autoimmune diseases.

The method of transplanting hemopoietic stem cells according to the present invention accomplishes the above-mentioned object. Particularly, by using the method of the present invention, the incidence of graft failure or rejection can be drastically reduced and the graft cells be well sustained, thus, allowing the transplant to express its intrinsic effect to achieve the s objectives: hemoimmunological recovery through normalization of hemopoiesis in the recipient and contribution to the treatment of chronic myelocytic leukemia (CML), acute myelocytic leukemia (AML), acute lymphocytic leukemia (ALL), malignant lymphoma, multiple myeloma, aplastic anemia gravis, myelodysplastic syndrome (MDS) and other hereditary diseases, treatment of autoimmune diseases, and gene therapy by the gene transfer technique.

The hemopoietic stem cells to be transplanted by the method of the present invention are not particularly restricted but may, for example, be those cells which are used in the conventional hemopoietic stem cell transplantation. More particularly, the cells may be bone marrow cells including hemopoietic stem cells, peripheral blood cells (particularly peripheral blood cells including hemopoietic stem cells as recruited by administration of a cytokine such as granulocyte colony-stimulating factor (G-CSF), cord blood cells, and mixtures of such cells. The typically preferred hemopoietic stem cells are bone marrow cells.

The donor of hemopoietic stem cells is not particularly restricted, either, but can be judiciously selected according to the criteria generally used when the transplantation of hemopoietic stem cells is considered appropriate to the recipient (patient).

The procedures for harvest and isolation of such hemopoietic stem cells are well known to those skilled in the art and not different from the procedures used in the conventional hemopoietic stem cell transplantation.

The hemopoietic stem cells which are particularly preferred for the purposes of the present invention may for example be bone marrow cells supplemented with about 1–2% of T cells from the standpoint of enhancing the graft rate without eliciting the onset of GVHD. More particularly, hemopoietic stem cells for transplantation are generally prepared by adding the usual anti-T cell antibody (e.g. a mixture of anti-CD3 antibody or anti-CD4 antibody with anti-CD8 antibody) to a cell population and then adding the complement to kill the cells (T cells) coupled to the anti-T cell antibody and thereby remove the T cells from the population or by adding anti-T cell antibody and removing the cells coupled to the anti-T cell antibody selectively by the magnetic bead method. The purification (isolation) of T cells can be made by removing erythrocytes from peripheral blood to provide mononuclear cells in the routine manner, adding said anti-T cell antibody to this cell population and selectively recovering the cells coupled to the anti-T cell antibody by the magnetic bead method or by adding the anti-T cell antibody conjugated with a fluorescent dye to the mononuclear cell population and recovering the T cells with an automatic fluorescent separation hardware. The above-mentioned preferred bone marrow cells for use in the present invention, that is to say bone marrow cells supplemented with a given concentration of T cells, can be prepared by mixing the T cells purified as above with the marrow cells depleted of T cells as above.

The most outstanding feature of the hemopoietic stem cell transplantation method of the present invention resides in two essential requirements, namely the radiation treatment using an effective dose for hemopoietic stem cell transplantation in advance and the subsequent portal venous administration of hemopoietic stem cells. As to the procedural details other than those two requirements, the conventional procedures for transplantation of hemopoietic stem cells apply.

For example, the hemopoietic stem cells to be administered into the portal vein can be prepared in a suitable dosage form (hereinafter referred to briefly as dosage form) in the same manner as the various pharmaceutical dosage forms containing cellular components of this type. Thus, except that they are administered into the portal vein, said hemopoietic stem cells can be used in the same manner as in the usual transplantation of hemopoietic stem cells. Where desired, said hemopoietic stem cells can be provided in the form of an injection.

In preparing the above dosage form, a variety of pharmaceutically acceptable carriers can be utilized. The carrier may be any of the carriers well known in the art. Furthermore, in preparing said dosage form, various infusions in common use today can also be employed. In addition, the dosage forms can be extemporaneously prepared from the donor in transplantation.

There is no particular limitation on the dose amount of said dosage form, either, but the dose amount conventionally used in the transplantation of hemopoietic stem cells can be employed. The preferred dosage may for example be about $3\times10^8$ marrow cells/kg or more.

It is important that the portal venous administration of said dosage form be carried out after the pre-transplantation irradiation.

The radiation treatment as the preparation for transplantation is carried out by irradiating the graft recipient with an effective radiation dose for hemopoietic stem cell transplantation. The "effective radiation dose" is characterized as an exposure dose frustrating recovery of the recipient's bone marrow cells (lethal dose) and is not particularly restricted as far as it is a medically acceptable dose which is generally used.

This radiation treatment can be carried out by total body irradiation (TBI) in the usual manner, preferably by the fractionated irradiation method using about 2 divided doses, for example a total radiation dose of about 10–12 Gy given in about 2 divided doses, particularly two fractional doses of 5–6 Gy each.

In one preferred embodiment of the present invention, hemopoietic stem cells are administered in a single dose from the portal vein, usually within about 24 hours of said irradiation. By this transplantation method, the graft failure or rejection of the donor-derived cells can be successfully avoided.

A still more preferred embodiment of the present invention comprises administering a supplemental dose of hemopoietic stem cells intravenously following the portal venous administration of hemopoietic stem cells. In accordance with this method, not only the graft failure or rejection of donor-derived cells can be more positively obviated but the radiation dose for use in the preparation for transplantation can be reduced.

Optionally, portal venous administration may be substituted for the above-mentioned intravenous administration for supplemental transplantation.

Inasmuch as it is performed after the initial portal venous administration of hemopoietic stem cells, the timing of this supplemental administration is not particularly restricted but this second administration is preferably carried out within about 5 days of the initial portal venous administration.

The procedure, as such, which can be used for said portal venous administration and for said intravenous administration of hemopoietic stem cells is well known to those skilled in the art. For example, the laparoscope-aided administration method which is per se known can be used for portal transplantation.

The above portal venous administration, preferably followed by said intravenous administration, after the radiation treatment according to the above-mentioned schedule results in a successful maintenance of the grafted hemopoietic stem cells in the recipient.

Unless the effect of the present invention is not compromised, the method of the present invention can be used in combination with the routine medical treatments given in the transplantation of hemopoietic stem cells as well as the chemotherapy with other drugs. The drugs which can be used in this concomitant chemotherapy include but are not limited to immunosuppressants such as cyclophosphamide (CY), cyclosporin A (CsA), methotrexate (MTX), and tacrolimus (FK506). Regarding the dosage and administration of such drugs, reference can be made to the corresponding information on the known (commercial) preparations.

BRIEF DESCRIPTION OF DRAWINGS

The following drawing is referred to in the following examples.

EXAMPLES

Figure 1:
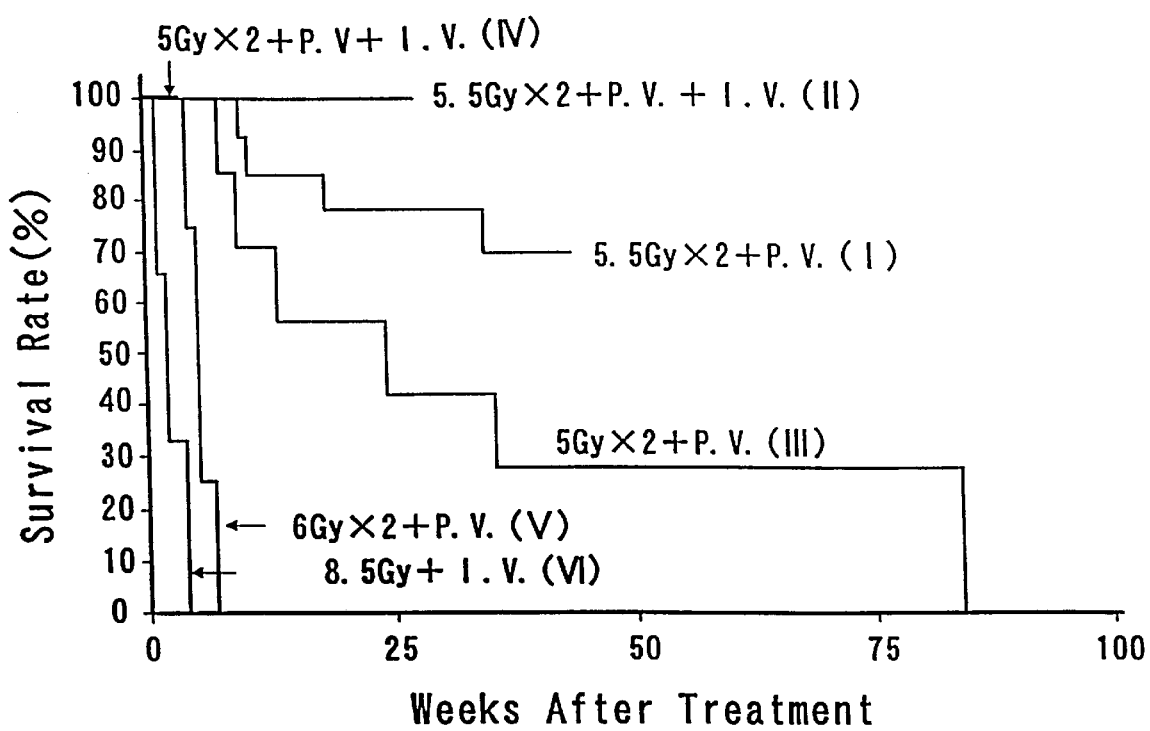
FIG. 1 is a diagram showing the data generated by the bone marrow transplantation performed in Test Example 1.

The following test examples and preparation examples, which are relevant to the method of the present invention, illustrate the invention in further detail.

Test Example 1
(1) Preparation of a Bone Marrow Cell Suspension

From a donor mouse, the femur and tibia were disconnected and a 22 G-needle (Code No. NN-2225RSS-02S, Terumo Co., Ltd.) attached to a syringe (2.5 ml, Code No. SS-02S, Terumo Co., Ltd.) was inserted into each bone from the knee joint side. The marrow cells were aspirated and, using the RPMI1640 solution contained in the syringe, flushed into a sterilized dish (90×15 mm, Iwaki Clinical Test Wares) and suspended in RPMI1640 solution. The harvested marrow cells were washed with RPMI1640 solution once and resuspended in the same solution to provide a bone marrow cell suspension (concentration $1\times10^8$ /ml).
(2) Removal of T Cells To a suspension of bone marrow cells in RPMI1640 solution (concentration $2\times10^7$ /ml) was added 1/10 of its volume of monoclonal anti-Thy-1.2 antibody (American Type Culture Collection, Rockvillge, Md.) and, after 30 minutes of standing at 4° C., washed with RPMI1640 solution once and readjusted to the concentration of $2\times10^7$/ml. As a complement source, rabbit serum (1/16 of the volume of the cell suspension) was added and the mixture was stirred in a constant-temperature bath at 37° C. for 30 minutes. It was then washed with RPMI1640 solution twice and adjusted to a concentration of $1\times10^8$/ml.

(3) Radiation Treatment

The radiation treatment of the recipient mouse was carried out by total body irradiation either in a single dose or in two divided doses with Gamma Cell 40 Exacter (Nordion International Inc.) using $^{137}$Cs as the beam source. In the case of fractionated irradiation in divided doses, an interval of 4 hours was provided between the first dose and the second dose. The irradiation was carried out on the day immediately preceding the portal venous injection or control intravenous injection.

(4) Portal Venous Injection

Under pentobarbital (Pitman-Moor Inc.; 37.5 mg/kg b. wt., i.p.) anesthesia, the recipient mouse was shaved of the hair coat with a razor and disinfected. After a midline incision was made in the abdominal region, the mesenterium was exposed and a 27 G needle (Terumo Co., Ltd.) attached to a 1 ml-tuberculin syringe was passed through the mesenteric adipose tissue, and $5\times10^7$ cells of the donor mouse bone marrow cells prepared above (0.5 ml of the suspension) were injected from the portal vein.

(5) Intravenous Injection

The donor mouse bone marrow cells were adjusted to $1\times10^8$/ml concentration and $5\times10^7$ cells (0.5 ml) were injected from the caudal vein of the recipient mouse.

(6) Bone Marrow Transplantation and Effect

The MRL/MP-lpr/lpr (MRL/lpr) mouse spontaneously develops lymphadenopathy with the accumulation of abnormal T cells and is known to be of use as an animal model of autoimmune disease such as systemic lupus erythematosus (SLE) or rheumatoid arthritis (RA).

A bone marrow transplantation was performed using such a MRL/lpr mouse (Japan SLC Inc.) as the recipient and a C57BL/6 mouse (B6, Japan SLC, Inc.) as the donor, and the survival of the recipient mouse and the graft of donor-derived cells were investigated. Moreover, the therapeutic effect on autoimmune disease was also investigated.

The bone marrow transplantation was carried out, after the predetermined radiation treatment, by injecting whole bone marrow cells (bone marrow cells not depleted of T cells; the same applies hereinafter) by the predetermined route or routes of administration.

The test groups provided were as follows:

Group I: Irradiation in 2 divided doses (5.5 Gy×2) and portal venous administration of whole bone marrow cells (n=13).

Group II: irradiation in 2 divided doses (5.5 Gy×2), portal venous administration of whole bone marrow cells, and intravenous administration of whole bone marrow cells 5 days after portal venous administration (n=10).

Group III: irradiation in 2 divided doses (5 Gy×2) and portal venous administration of whole bone marrow cells (n=7).

Group IV: irradiation in 2 divided doses (5 Gy×2), portal venous administration of whole bone marrow cells, and intravenous administration of whole bone marrow cells 5 days after portal venous administration (n=13).

Group V: irradiation in 2 divided doses (6 Gy×2) and portal venous administration of whole bone marrow cells (n=4).

Group VI: irradiation in a single dose (8.5 Gy) and intravenous administration of whole bone marrow cells (n=10).

The results are presented in FIG. 1. In FIG. 1, the ordinate represents survival rate (%) and the abscissa represents weeks after treatment. The groups are indicated by the respective group designations.

(7) Interpretation of the Data

For the purpose of treating autoimmune diseases which had developed, a bone marrow transplantation therapy was administered in MRL/lpr mice manifesting a proteinuria value of $\geq 2.5$ and lymphadenopathy.

When the conventional intravenous bone marrow transplantation (Group VI: control group) was performed, all the recipient MRL/lpr mice died within 4 weeks.

On the other hand, in the group which received the 5.5 Gy×2 radiation and portal venous administration of whole bone marrow cells (Group I), 71% of the recipient mice were still alive at 40 weeks after transplantation, indicating a high success rate. Furthermore, in those recipient animals, graft of donor-derived cells and cure of the autoimmune diseases were confirmed.

It was noteworthy that in the group treated with 5.5 Gy×2 irradiations, portal venous administration of whole bone marrow cells and intravenous administration of whole bone marrow cells 5 days after portal venous administration (Group II), all the animals were alive, with the autoimmune diseases cured, at 25 weeks following the transplantation.

Furthermore, in the test group receiving 5 Gy×2 doses of radiation (Group IV; the other treatment conditions were the same as in Group II), satisfactory results were obtained although the assessment was made just 5 weeks after transplantation, indicating that the combination of portal venous and intravenous administrations enables reduction in the necessary radiation exposure dose. In the group which received 5 Gy×2 irradiation and portal venous administration of whole bone marrow cells (Group III), all the mice had died by 80 weeks after transplantation but this survival period is equivalent to 96 weeks after birth and is substantially equal to the average life span of normal mice. The individuals which died within 30 weeks of treatment revealed no graft of donor-derived cells and were thought to have died because of progression of the autoimmune diseases. It was, therefore, suggested that the individuals with successful graft were allowed to live long. It appeared that the 5 Gy×2 radiation is a critical dose for substitution of the hemopoietic and immune cells of the host for the donor cells and, therefore, that the supplemental intravenous administration after portal venous administration (Group IV) meets with success.

On the other hand, in the group treated with 6 Gy×2 irradiation and portal venous administration of whole bone marrow cells (Group V), all the animals had died by 7 weeks after transplantation, suggesting that the mice could not withstand the invasion of radiation. It was, thus, found that the 6 Gy×2 irradiation is unsuited for radiation-sensitive mice such as MRL/lpr mice. However, it has been found that the 6 Gy×2 irradiation is the optimal dose for mice of strains other than MRL/lpr.

(8) Discussion

The MRL/lpr mouse is susceptible to radiation on the individual level and this tendency is observed more prominently after onset of autoimmune disease. However, at the cellular level, this mouse has radiation-resistant hemopoietic stem cells and, therefore, treatment of autoimmune disease in MRL/lpr mice by bone marrow transplantation has heretofore been extremely difficult. In accordance with the present invention, the proper irradiation and subsequent portal venous administration result in improved or early graft of donor marrow cells. Thus, a method of treating autoimmune diseases even in MRL/lpr mice could be established.

It is evident from the foregoing results that an immunological tolerance to donor cells can be induced in the recipient by the above treatment of the present invention. Therefore, the long-term use of immuno-suppressants, which was essential for the conventional bone marrow transplantation through intravenous administration of marrow cells, can now be dispensed with and, accordingly, the physical burden on the patient can be reduced. Furthermore, laparoscope-guided portal venous administration is a well-established and safe technique which can be performed without opening of the abdomen, thus lessening the burden on the patient in this aspect as well.

Therefore, it is concluded that the present invention is useful for the therapy of diseases in which bone marrow transplantation is indicated, such as autoimmune diseases in humans.

Preparation Example 1

Bone marrow cells are suspended in physiological saline to provide a cell suspension of $1 \times 10^8$ cells/ml. Generally, for portal venous administration to a human, the recommended dose is not less than $3 \times 10^8$ bone marrow cells per kilogram body weight. Therefore, an injection is prepared in a dosage form at least containing the above dose.

Preparation Example 2

A $1 \times 10^8$ cells/ml suspension of bone marrow cells depleted of T cells as prepared using anti-T cell antibody (a mixture of anti-CD3 antibody or anti-CD4 antibody with anti-CD8 antibody) is mixed with about 1–2% of T cells prepared from peripheral blood using said antibody and an injection for portal venous administration is prepared.

What is claimed is:

1. A method of transplanting hemopoietic stem cells in a recipient afflicted with an autoimmune disease, comprising the steps of:
    (a) subjecting the recipient to a radiation treatment that is lethal to the recipient's bone marrow cells but not to the recipient, the radiation treatment comprising two doses of total body irradiation each in a range of 5 to 5.5 Gy, followed by;
    (b) transplanting hemopoietic stem cells from a donor to the recipient by portal venous administration, and
    (c) transplanting hemopoietic stem cells from the donor to the recipient by intravenous administration.

2. The method according to claim 1, wherein the two doses of total body irradiation are carried out at an interval of about four hours.

* * * * *